United States Patent
Purpura et al.

(10) Patent No.: US 10,959,957 B2
(45) Date of Patent: Mar. 30, 2021

(54) STABILIZATION OF BETA-HYDROXYISOVALERIC ACID FORMULATIONS IN SOFT GEL CAPSULES

(71) Applicant: TSI Group Ltd., Missoula, MT (US)

(72) Inventors: Martin Purpura, Austin, TX (US); Ralf Jager, Milwaukee, WI (US); Jie Gu, Shanghai (CN); Xiong Zheng, Shanghai (CN); Iingwei Dai, Shanghai (CN); Yaohua Zhang, Shangahi (CN)

(73) Assignee: TSI Group Ltd., Missoula, MT (US)

( * ) Notice: Subject to any disclaimer, the term of this patent is extended or adjusted under 35 U.S.C. 154(b) by 0 days.

(21) Appl. No.: 15/605,664

(22) Filed: May 25, 2017

(65) Prior Publication Data

US 2017/0340572 A1 Nov. 30, 2017

Related U.S. Application Data

(60) Provisional application No. 62/341,464, filed on May 25, 2016.

(51) Int. Cl.
*A61K 9/48* (2006.01)
*A61K 31/19* (2006.01)

(52) U.S. Cl.
CPC .......... *A61K 9/4816* (2013.01); *A61K 9/4858* (2013.01); *A61K 9/4866* (2013.01); *A61K 31/19* (2013.01)

(58) Field of Classification Search
None
See application file for complete search history.

(56) References Cited

U.S. PATENT DOCUMENTS

| | | | |
|---|---|---|---|
| 2,870,062 A | 1/1959 | Stanley et al. | |
| 5,200,191 A | 4/1993 | Steele et al. | |
| 5,569,466 A | 10/1996 | Tanner et al. | |
| 7,011,846 B2 | 3/2006 | Shojaei et al. | |
| 8,231,896 B2 * | 7/2012 | Tanner ................. | A61K 9/4816 424/451 |
| 9,980,916 B2 * | 5/2018 | Fang ......................... | A61J 3/07 |
| 10,188,611 B2 * | 1/2019 | White .................. | A61K 9/4816 |
| 2003/0091615 A1 * | 5/2003 | Craig ................... | A61K 31/205 424/439 |
| 2004/0006139 A1 | 1/2004 | Jager et al. | |
| 2005/0175763 A1 | 8/2005 | Purpura et al. | |
| 2008/0020995 A1 | 1/2008 | Purpura et al. | |
| 2008/0031964 A1 | 2/2008 | Messadek | |
| 2012/0053240 A1 * | 3/2012 | Rathmacher ........... | A61K 31/19 514/557 |
| 2013/0337144 A1 | 12/2013 | Lai et al. | |
| 2014/0080781 A1 | 3/2014 | Baier et al. | |
| 2014/0272000 A1 | 9/2014 | Baier et al. | |
| 2015/0342914 A1 | 12/2015 | Zemel et al. | |
| 2015/0366813 A1 * | 12/2015 | Thakur .............. | A61K 31/4439 424/452 |
| 2016/0038425 A1 | 2/2016 | Fang et al. | |

FOREIGN PATENT DOCUMENTS

| | | | | |
|---|---|---|---|---|
| EP | 1105107 A1 | 6/2001 | | |
| WO | 9636320 | 11/1996 | | |
| WO | 2003071884 A1 | 9/2003 | | |
| WO | 2006122809 A1 | 11/2006 | | |
| WO | WO-2014152098 A1 * | 9/2014 | ............... | A61K 8/02 |
| WO | 2015094925 A1 | 6/2015 | | |

* cited by examiner

*Primary Examiner* — Celeste A Roney

(74) *Attorney, Agent, or Firm* — Davis, Brown, Koehn, Shors & Roberts, P.C.; Matthew Coryell

(57) ABSTRACT

The disclosed are shelf-stable beta-hydroxyisovaleric acid containing soft gel compositions and methods for making such compositions. In certain aspects, disclosed compositions comprise a plant-based capsule shell and a liquid formulation comprising beta-hydroxyisovaleric acid and at least one excipient, wherein the soft gel capsule is shelf-stable. In certain aspects, the excipient is selected from selected from choline salt, betaine, phosphatidylcholine, alpha-glycerophosphocholine, carnitine, adenosine 5'-triphosphate, or a combination thereof.

20 Claims, No Drawings

STABILIZATION OF BETA-HYDROXYISOVALERIC ACID FORMULATIONS IN SOFT GEL CAPSULES

CROSS-REFERENCE TO RELATED APPLICATION(S)

This application claims priority to U.S. Provisional Application No. 62/341,464, filed May 25, 2016 and entitled "Stabilization of Beta-Hydroxyisovaleric Acid Formulations In Soft Gel Capsules," and hereby incorporates the same by reference in its entirety.

TECHNICAL FIELD

The disclosure relates to a composition and related methods of production for a soft gel capsule comprising a capsule shell and a liquid formulation of HMB-FA and at least one excipient.

BACKGROUND

Beta-hydroxyisovaleric acid in its free acid form, interchangeably referred to herein as "HMB-FA", is also known in the art as 3-Hydroxy-3-Methylbutyric acid, β-Hydroxy-β-Methylbutyric acid, 3-Hydroxy-3-methylbutyrate, β-Hydroxy-β-methylbutyrate, β-Hydroxy-β-methylbutyrate, 3-Hydroxy-3-Methylbutanoic acid, and β-Hydroxy-β-Methylbutanoic acid. The molecule, shown below, has a structural formula of $(CH_3)_2C(OH)CH_2COOH$:

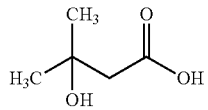

HMB is known to improve nitrogen retention and protein sparing, improve lean body mass, improve muscle function and/or muscle performance, decrease muscle damage in muscle subjected to stress or damage, decrease inflammatory response after muscle is subjected to stress or damage, improve the body's immune response after stress or damage, treat disease associated wasting (such as wasting associated with cancer, chronic pulmonary disease, age, chronic kidney disease, long-term hospitalization or AIDS), improve a lipid profile such a low density lipoprotein (LDL) to high density lipoprotein (HDL), and improve a person's emotional state.

Currently, HMB-FA is administered by soft gel capsules, where it is incorporated into the gel capsule its pure liquid form. However, the hygroscopic character of HMB-FA causes water migration from or through the capsule shell during the manufacture, drying, and storage of the gel capsules. The water migration results in deterioration of the gel capsule because many capsule shell materials, including gelatin, carrageenan, hydroxypropyl methyl cellulose, pullulan, or mixtures thereof, and plasticizers, have a critical moisture content at which the soft gel capsule maintains integrity and stability. Water migration changes the moisture content of both the capsule shell and the filling, which either leads to cracking and failure as the water migrates from the capsule shell to the filling or to softening of the capsule shell as environmental water migrates into the gel capsule.

There is a need in the art for a gel capsule filling composition that can overcome the issues arising from the high hygroscopy of HMB-FA. The disclosed soft gel capsule filling composition of HMB-FA and at least one excipient was surprisingly and unexpectedly found to solve the stability issues arising from high hygroscopy of HMB-FA.

BRIEF SUMMARY

Described herein are various embodiments relating to a composition and related methods of production for a soft gel capsule comprising a capsule shell and a liquid formulation of beta-hydroxyisovaleric acid and at least one excipient.

In certain aspects, the excipient is selected from choline salt, betaine, phosphatidylcholine, alpha-glycerophosphocholine, carnitine, adenosine 5'-triphosphate, or a combination thereof. In further aspects, the capsule shell comprises at least one shell material selected from carrageenan, hydroxypropyl methyl cellulose, pullulan, or a combination thereof.

In further aspects, the liquid formulation comprises between about 40 wt % and about 80 wt % beta-hydroxyisovaleric acid. In still further aspects, the liquid formulation comprises between about 10 wt % and about 60 wt % excipient.

According to certain further aspects, the liquid formulation further comprises water. In exemplary aspects, the liquid formulation comprises between about 0.1 wt % and about 7 wt % water.

Further disclosed herein is a soft gel capsule that comprises a capsule shell; and a liquid formulation comprising beta-hydroxyisovaleric acid and betaine anhydrous, wherein the soft gel capsule is shelf-stable. In certain aspects, the capsule shell is comprised of a plant-based composition that is comprised of at least one of carrageenan, hydroxypropyl methyl cellulose, pullulan, or a combination thereof. In further aspects, the capsule shell is substantially free of animal-derived compositions. In certain further aspects, the liquid formulation comprises between about 50 wt % and about 85 wt % beta-hydroxyisovaleric acid. In still further aspects, the liquid formulation comprises between about 10 wt % and about 25 wt % betaine anhydrous.

According to certain further embodiments, the soft gel further comprises at least one additional excipient selected from choline salt, phosphatidylcholine, alpha-glycerophosphocholine, carnitine, adenosine 5'-triphosphate, or combinations thereof. In exemplary embodiments, the at least one additional excipient is between about 5 wt % and about 20 wt %.

According to certain further aspects, the liquid formulation further comprises water. In exemplary aspects, the concentration of the water is between about 0.1 wt % and about 7 wt %.

Further disclosed herein is a method for producing a soft gel capsule, comprising the steps of: providing a plant-derived capsule shell; mixing a liquid formulation comprising beta-hydroxyisovaleric acid and at least one excipient, wherein the beta-hydroxyisovaleric acid and the at least one excipient are mixed using an agitator, an in-inline mixer or by jet mixing; and incorporating the liquid formulation into the capsule shell.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure.

Accordingly, the drawings and detailed description are to be regarded as illustrative in nature and not restrictive.

DETAILED DESCRIPTION

Although the disclosure has been described with reference to preferred embodiments, persons skilled in the art will recognize that changes may be made in form and detail without departing from the spirit and scope of the disclosed invention.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. Unless otherwise defined, all technical and scientific terms used herein have the same meaning as commonly understood by one of ordinary skill in the art to which this invention belongs.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "effective dose" or "effective amount" refers to an amount effective, at dosages and for periods of time necessary, to achieve the desired result.

A weight percent (wt. %) of a component, unless specifically stated to the contrary, is based on the total weight of the formulation or composition in which the component is included.

As used herein, the term "shelf-stable" means capable of being stored at room temperature (e.g., about 20° C. to about 25° C.) for long periods (e.g., 3 months or more) without a substantial degradation of HMB-FA and without substantial degradation of the physical characteristics of the capsule.

This disclosure relates to a composition and related methods of production of a soft gel capsule comprising a capsule shell and a liquid formulation of HMB-FA and at least one excipient, wherein the soft gel capsule has a positive increase in shelf-stability over current commercially available products.

In certain aspects the disclosed soft gel capsule comprises a capsule shell and a liquid formulation comprising HMB-FA and at least one excipient, wherein the soft gel capsule is shelf-stable. In certain aspects the excipient is selected from selected from choline salt, betaine, phosphatidylcholine, alpha-glycerophosphocholine, carnitine, adenosine 5'-triphosphate, or a combination thereof. In further aspects, the excipient is betaine. In further aspects, the excipient is L-Carnitine.

According to certain aspects, the capsule shell is comprised of a plant-derived substance. In exemplary embodiments, the plant-derived substance is a polysaccharide. In further aspects, the capsule shell selected from carrageenan, hydroxypropyl methyl cellulose, pullulan, or a combination thereof. In still further aspects, the capsule shell is substantially free of gelatin. In yet further aspects, the capsule shell is substantially free of animal-derived products.

In certain aspects, the disclosed soft gel capsule comprises a liquid formulation comprising between about 40 wt % and about 80 wt % HMB-FA. According to still further aspects, the soft gel comprises between about 50 wt % and about 80 wt % HMB-FA.

In certain exemplary embodiments, the liquid formulation comprises between about 10 wt % and about 60 wt % excipient. According to certain alternative embodiments, the liquid formulation comprises between about 10 wt % and about 50 wt % excipient. In yet further embodiments, the liquid formulation comprises between about 10 wt % and about 40 wt % excipient. In even further embodiments, the liquid formulation comprises between about 10 wt % and about 30 wt % excipient. In yet further embodiments, the liquid formulation comprises between about 10 wt % and about 20 wt % excipient. According to certain embodiments, the liquid formulation comprises about 18% excipient.

According to certain aspects, the liquid formulation further comprises water. In exemplary embodiments, the liquid formulation comprises between about 0.1 wt % and about 7 wt % water.

In certain aspects, the soft gel capsule is shelf-stable for at least three months. In further aspects, the soft gel capsule is shelf-stable for at least six months. In still further aspects, the soft gel capsule is shelf-stable for at least about two years.

Further disclosed herein is a soft gel capsule comprising a capsule shell; and a liquid formulation comprising beta-hydroxyisovaleric acid and betaine anhydrous, wherein the soft gel capsule is shelf-stable. In certain aspects, capsule shell comprises at least one of carrageenan, hydroxypropyl methyl cellulose, pullulan, or a combination thereof. In certain exemplary aspects, the capsule shell is substantially free of animal-derived compositions.

According to exemplary embodiments, the liquid formulation is comprised of between about 50 wt % and about 85 wt % HMB-FA and between about 15 wt % and about 25 wt % betaine anhydrous. In certain exemplary embodiments, the liquid formulation comprises between about 10 wt % and about 60 wt % betaine anhydrous. According to certain alternative embodiments, the liquid formulation comprises between about 10 wt % and about 50 wt % betaine anhydrous. In yet further embodiments, the liquid formulation comprises between about 10 wt % and about 40 wt % betaine anhydrous. In even further embodiments, the liquid formulation comprises between about 10 wt % and about 30 wt % betaine anhydrous. In yet further embodiments, the liquid formulation comprises between about 10 wt % and about 20 wt % betaine anhydrous. According to certain embodiments, the liquid formulation comprises about 18 wt % betaine anhydrous.

According to further exemplary embodiments, the capsule further comprises at least one additional excipient. In certain aspects of these exemplary embodiments, the at least one additional excipient is selected from choline salt, phosphatidylcholine, alpha-glycerophosphocholine, carnitine, adenosine 5'-triphosphate, or combinations thereof. In certain aspects, the at least one additional excipient is present at an amount of between about 5 wt % and about 20 wt %.

According to certain further embodiments, the liquid formulation contained within the soft gel capsule further comprises water. In certain aspects, water is present in an amount of between about 0.1 wt % and about 7 wt % of the liquid formulation. In certain aspects, the water is purified water.

In preferred embodiments, the liquid formulation of the soft gel capsule composition contains an effective amount of HMB-FA and an excipient to positively affect the shelf-life stability rate and integrity of the capsule shell. In certain embodiments, the liquid formulation comprises at least 40 wt % of beta-hydroxyisovaleric acid and at least 20 wt % excipient.

According to certain embodiments, the disclosed soft gel capsules contain an amount of HMB-FA effective to promote muscle growth when administered to a subject. According to further embodiments, the disclosed soft gel capsules contain an amount of HMB-FA effective to increase muscle healing after damage. According to still further embodiments, the disclosed soft gel capsules contain an amount of HMB-FA effective to prevent cachexia such as that suffered by patients with cancer or HIV/AIDS. In still further embodiments, the disclosed soft gel capsules contain an amount of HMB-FA effective to prevent sarcopenia. According to certain embodiments, the disclosed soft gel capsules contains from between about 200 mg to about 1000 mg/capsule of HMB-FA. In still further embodiments, the disclosed soft gel capsules contains about 500 mg/capsule of HMB-FA.

Further disclosed herein is a method for producing a soft gel capsule comprising the steps of providing a capsule shell, mixing a liquid formulation comprising HMB-FA and at least one excipient, and incorporating the liquid formulation into the capsule shell.

According to certain aspects, the components of the liquid formulation are mixed using an agitator, in-line mixer, or by jet mixing. In certain further aspects, the liquid formulation is incorporated into the capsule shell using a plate process, rotary die process, reciprocating die process, or an accogel machine process. According to further aspects, mixing is performed by way of a batch process. In certain alternative embodiments, mixing is achieved by way of a continuous process.

In certain embodiments of the disclosed method, the capsule shell comprises at least one of gelatin, carrageenan, hydroxypropyl methyl cellulose, pullulan, or a combination thereof. In further embodiments, the capsule shell further comprises plasticizers, including but not limited to glycerol, sorbitol, xylitol, sorbitol, polyglycerol. A person of skill in the art would appreciate that other materials can be used in capsule shell formulations.

In certain embodiments, the excipient is selected from choline salt, betaine, phosphatidylcholine, alpha-glycerophosphocholine, carnitine, adenosine 5'-triphosphate, or a combination thereof. In further embodiments, the at least one excipient is betaine anhydrous. In certain exemplary embodiments, one or more additional excipients is present and is selected from choline salt, phosphatidylcholine, alpha-glycerophosphocholine, carnitine, adenosine 5'-triphosphate, or a combination thereof.

In various embodiments, the liquid formulation can be mixed using an agitator, jet mixing, or in-inline mixer, including, but not limited to, a high speed shearing mixer. Mixing can be completed in a batch or continuous process. In further embodiments, the liquid formulation can be incorporated into soft gel capsules by using a plate process, rotary die process, reciprocating die process, accogel machine process, or any other similar process.

The various embodiments disclosed above yielded an unexpected and surprising positive increase in the shelf-life stability of the soft gel capsule. Thus, the disclosed invention addresses a need in the art for shelf-stable soft gel capsules for HMB-FA delivery.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Blending or mixing procedure for the filling formulation. Formulations as outlined in Table 1 were mixed with liquid beta-hydroxyisovaleric acid by using a high shear mixer. The weight percentage in Table 1 refers to the residual amount in liquid beta-hydroxyisovaleric acid, for example, when betaine anhydrous was used in a concentration of 20 wt %, beta-hydroxyisovaleric acid was used in a concentration of 80 wt %.

TABLE 1

Exemplary Formulations

| Excipient | Weight Percentage [%] |
|---|---|
| Betaine Anhydrous | 20 |
| Betaine Anhydrous | 25 |
| Choline Chloride | 43 |
| L-Carnitine | 47 |
| L-Carnitine | 25 |
| alpha-Glycerophosphocholine | 25 |
| alpha-Glycerophosphocholine | 20 |
| alpha-Glycerophosphocholine | 58 |
| Betaine Anhydrous + Choline Chloride | 10 + 10 |
| Betaine Anhydrous + L-Carnitine | 10 + 10 |
| Phosphatidylcholine | 25 |
| Adenosine 5'-triphosphate | 34 |

Results: The residual moisture content of the HMB-FA plus excipient formulations never exceeded 5%.

Example 2

Encapsulation trials were conducted using polysaccharide-based capsule shells in combination with the different fill formulations from Example 1. Commercially available gelatin-free capsule shells were used. The gelatin-free soft gel capsules were produced using a commercial available rotary-die encapsulation process.

Example 3

Shelf-Life Stability Test: After incorporating the soft gel capsules from Example 2 with the liquid formulations from Example 1, shelf-life stability tests were conducted. The test conditions for such physical stability tests were at room temperature in an open container. Soft gel capsules were observed periodically for effects such as: softness, tackiness, bloatedness, brittleness, breakage, and leakage. The integrity of all manufactured soft capsules was studied for 90 days. The results, taken as a whole, showed self-life stability was superior for gel capsules prepared with polysaccharide-based capsules compared with those prepared with commercially available gelatin-based capsules.

Example 4

To test the ability of plant-based (polysaccharide) soft gels to maintain long-term shelf stability, accelerated stability tests were performed. As shown in Table 2 below, plant-based polysaccharide soft gels maintained a high degree of stability in the accelerated stability test.

TABLE 2

Accelerated Stability Test

| Time Interval | Change of appearance | Level of Adhesion (between capsules) | Leakage |
| --- | --- | --- | --- |
| 1 month | No Obvious Change | Very Slight | None |
| 2 months | No Obvious Change | Slight | None |
| 3 months | No Obvious Change | Noticeable | None |

Example 5

Accelerated Stability Test: To assess how the quality and purity of the instantly disclosed composition would vary with time under the influence of environmental factors of temperature and humidity, accelerated stability tests were performed. Tests were carried out according to guidelines provided in Stability Testing of New Drug Substances and Products issued by ICH and Stability testing guideline of dietary supplements by NSF. *NSF Stability Testing Working Group, Stability testing guideline of dietary supplements*, January 2011. Briefly, samples prepared according to the methods disclosed herein and had a HMB-FA contents of between about 475-525 mg/capsule. The gel capsule composition was HMB-FA 75 wt %; betaine anhydrous 18 wt % and purified water 7 wt %. Samples were repacked in HDPE bottles (size: 1 80 ct, 300 ml) then sealed with aluminum foil. Samples were exposed to high temperature and high humidity (40±2° C.; 75% RH±5% RH) and evaluated at 1, 2, and 3 months. The results are presented in Table 3.

TABLE 3

HMB-FA Contents Following Accelerated Stability Tests

| | | Time Interval (months) | | | |
| --- | --- | --- | --- | --- | --- |
| | Input Dose | 0 | 1 | 2 | 3 |
| HMB FA (mg/capsule) | 510 | 519 | 494.4 | 484.8 | 491.8 |

The foregoing results indicate that HMB FA is substantially stable, at even high heat high humidity environments for periods exceeding three months. As set forth in Table 4, the physical characteristics of the soft gels following the accelerated stability test showed high levels of stability after three months of high heat high humidity conditions. Extrapolating from the accelerating stability tests, these results indicate that soft gel compositions of the instant disclosure are shelf-stable for up to 2 years when stored at room temperature conditions.

TABLE 4

Physical Characteristics Contents Following Accelerated Stability Tests

| | Trial 1 (40° C. ± 2° C./ 75% RH ± 5% RH) | | | Trial 2 (37° C. ± 2° C./ 7 5% RH ± 5% RH) | | |
| --- | --- | --- | --- | --- | --- | --- |
| | 1 month | 2 months | 3 months | 1 month | 2 months | 3 months |
| Change in Appearance | No | No | No | No | No | No |
| Level of Adhesion | Very Slight | Very Slight | Noticeable | Very Slight | Very Slight | Slight |
| Leakage | No | No | No | No | No | No |

The following references, to the extent that they provide exemplary procedural or other details supplementary to those set forth herein, are specifically incorporated herein by reference. Patent Cooperation Treaty Application Serial No. PCT/CN2013/088762 filed Dec. 6, 2013 and Chinese Application No. CN 201310127262 filed Apr. 12, 2013, which relate to novel methods for purification of β-hydroxyl-β-methylbutyrate.

What is claimed is:

1. A soft gel capsule comprising:
   a. a capsule shell; and
   b. a liquid formulation comprising at least about 40% 3-hydroxy-3-methylbutyric acid and at least one excipient selected from the group consisting of: choline salt, betaine, phosphatidylcholine, alpha-glycerophosphocholine, carnitine, adenosine 5'-triphosphate, or a combination thereof, and wherein the soft gel capsule is shelf-stable.

2. The soft gel capsule of claim 1, wherein the capsule shell comprises at least one shell material selected from carrageenan, hydroxypropyl methyl cellulose, pullulan, or a combination thereof.

3. The soft gel capsule of claim 1, wherein the capsule shell is gelatin free.

4. The soft gel capsule of claim 1, wherein the liquid formulation comprises between about 40 wt % and about 80 wt % 3-hydroxy-3-methylbutyric acid.

5. The soft gel capsule of claim 1, wherein the liquid formulation comprises between about 10 wt % and about 60 wt % excipient.

6. The soft gel capsule of claim 1, wherein the liquid formulation further comprises from about 0.1 wt % to about 5 wt % water.

7. The soft gel capsule of claim 1, wherein the soft gel capsule is shelf-stable for at least six months.

8. A soft gel capsule comprising
   a. a capsule shell; and
   b. a liquid formulation comprising at least 3-hydroxy-3-methylbutyric acid and betaine anhydrous, wherein the soft gel capsule is shelf-stable.

9. The soft gel capsule of claim 8, wherein the capsule shell comprises at least one of carrageenan, hydroxypropyl methyl cellulose, pullulan, or a combination thereof.

10. The soft gel capsule of claim 9, wherein the capsule shell is free of animal-derived compositions.

11. The soft gel capsule of claim 8, wherein the liquid formulation comprises between about 50 wt % and about 85 wt % 3-hydroxy-3-methylbutyric acid.

12. The soft gel capsule of claim 8, wherein the liquid formulation comprises between about 10 wt % and about 25 wt % betaine anhydrous.

13. The soft gel capsule of claim 12, further comprising at least one excipient selected from choline salt, phosphatidylcholine, alpha-glycerophosphocholine, carnitine, adenosine 5'-triphosphate, or combinations thereof.

14. The soft gel capsule of claim 13, wherein the concentration of the at least one excipient is between about 5 wt % and about 20 wt %.

15. The soft gel capsule of claim 8, wherein the liquid formulation further comprises water.

16. The soft gel capsule of claim 15, wherein the concentration of the water is between about 0.1 wt % and about 7 wt %.

17. The soft gel capsule of claim 8, wherein the soft gel capsule is shelf-stable for up to at least six months.

18. A method for producing a soft gel capsule, comprising the steps of:
  a. providing a plant-derived capsule shell;
  b. mixing a liquid formulation comprising 3-hydroxy-3-methylbutyric acid and at least one excipient, wherein the 3-hydroxy-3-methylbutyric acid and the at least one excipient are mixed using an agitator, an in-inline mixer or by jet mixing; and
  c. incorporating the liquid formulation into the capsule shell.

19. The soft gel capsule of claim 1, wherein the combination of 3-hydroxy-3-methylbutyric acid and the excipient prevents migration of water through the capsule shell.

20. The soft gel capsule of claim 8, wherein the combination of 3-hydroxy-3-methylbutyric acid and the betaine anhydrous prevents migration of water through the capsule shell.

* * * * *